United States Patent
van der Houwen et al.

(10) Patent No.: US 8,944,063 B2
(45) Date of Patent: Feb. 3, 2015

(54) TRACHEOSTOMA VALVE

(75) Inventors: Eduard Berend van der Houwen, Groningen (NL); Gijsbertus Jacobus Verkerke, Glimmen (NL); Bernandus Franciscus Augustinus Maria van der Laan, Haren (NL)

(73) Assignees: Academisch Ziekenhuis Groningen, Groningen (NL); Rijksuniversiteit Groningen, Groningen (NL)

( * ) Notice: Subject to any disclaimer, the term of this patent is extended or adjusted under 35 U.S.C. 154(b) by 785 days.

(21) Appl. No.: 13/262,465

(22) PCT Filed: Mar. 31, 2010

(86) PCT No.: PCT/NL2010/050165
§ 371 (c)(1),
(2), (4) Date: Dec. 23, 2011

(87) PCT Pub. No.: WO2010/114372
PCT Pub. Date: Oct. 7, 2010

(65) Prior Publication Data
US 2012/0090621 A1 Apr. 19, 2012

Related U.S. Application Data

(60) Provisional application No. 61/180,956, filed on May 26, 2009.

(30) Foreign Application Priority Data

Apr. 1, 2009 (EP) ..................................... 09157110

(51) Int. Cl.
  *A61M 16/00* (2006.01)
  *A61M 16/04* (2006.01)
(52) U.S. Cl.
  CPC ................................ *A61M 16/0468* (2013.01)
  USPC ................................................... 128/207.16
(58) Field of Classification Search
  CPC ...................... A61M 16/0468; A61M 16/0465
  USPC ............. 128/207.16, 207.14, 200.26, 207.15, 128/207.29, 200.24; 623/9
  See application file for complete search history.

(56) References Cited

U.S. PATENT DOCUMENTS 3,747,127 A    7/1973  Taub
4,582,058 A *  4/1986  Depel et al. .............. 128/207.17

(Continued)

FOREIGN PATENT DOCUMENTS

| EP | 0 078 685 | 5/1983 |
| EP | 1 025 874 | 8/2000 |
| WO | WO 03/061531 A2 | 7/2003 |

OTHER PUBLICATIONS

International Searching Authority/European Patent Office, "International Search Report," for PCT/NL2010/050165, mailed Jan. 28, 2011, 5 pages.

(Continued)

*Primary Examiner* — Lynne Anderson
*Assistant Examiner* — Bradley Philips
(74) *Attorney, Agent, or Firm* — Haynes and Boone, LLP

(57) ABSTRACT

A tracheostoma valve (1) comprises a main air passage structure provided with a main valve arrangement. The tracheostoma valve is switchable in response to a spurt of inhalation air from a breathing condition into a speaking condition, while the tracheostoma valve is switchable in response to a spurt of exhalation air from said speaking condition into said breathing condition. The main valve arrangement comprises an at least partly flexible bistable wall portion which has a circumferential bordering edge. At least part of the bordering edge forms a hinging means around which the bistable wall portion is hingeable between a first stable position in which an orifice of the main air passage structure is being blocked, and a second stable position in which said orifice is released.

9 Claims, 6 Drawing Sheets

(56) References Cited

U.S. PATENT DOCUMENTS

| | | | | |
|---|---|---|---|---|
| 5,392,775 | A | * | 2/1995 | Adkins et al. ............ 128/207.16 |
| 6,439,233 | B1 | * | 8/2002 | Geertsema ............... 128/207.16 |
| 6,921,417 | B2 | * | 7/2005 | Persson ............................. 623/9 |
| 2004/0089291 | A1 | * | 5/2004 | Persson ................... 128/200.16 |
| 2005/0178390 | A1 | * | 8/2005 | Worthington ............ 128/207.16 |

OTHER PUBLICATIONS

European Office Action received in corresponding European Patent Application No. 10711094.2-1662, dated Oct. 30, 2013, 6 pages.

* cited by examiner

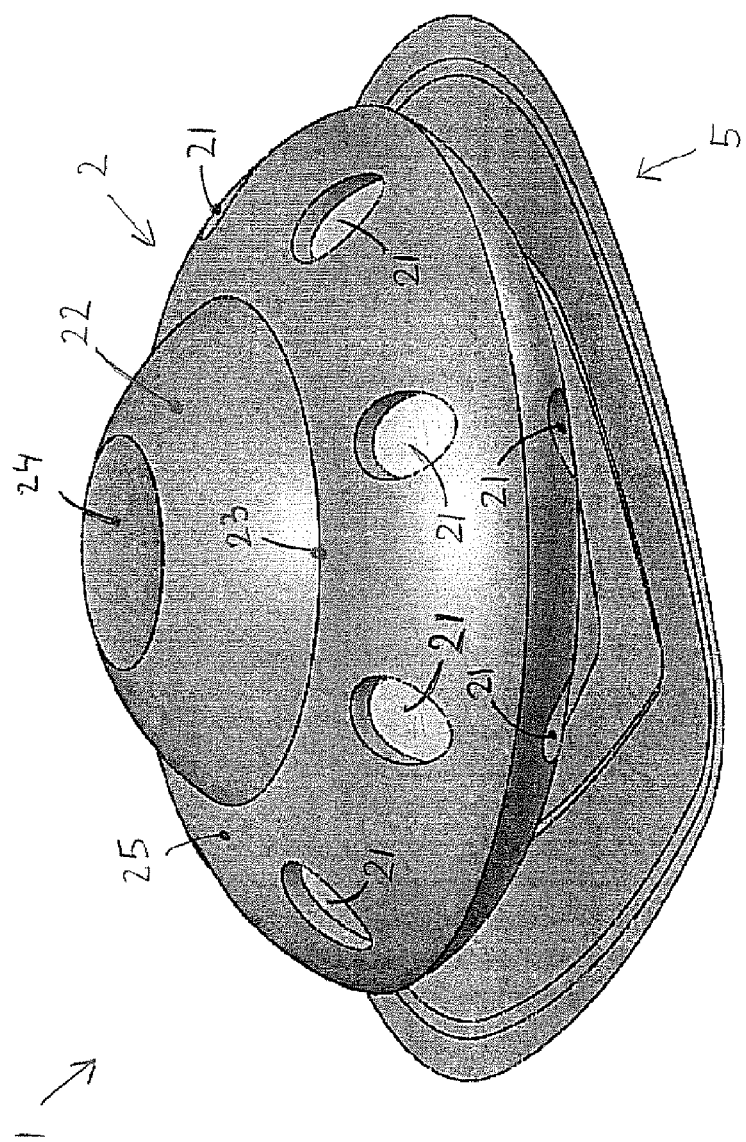

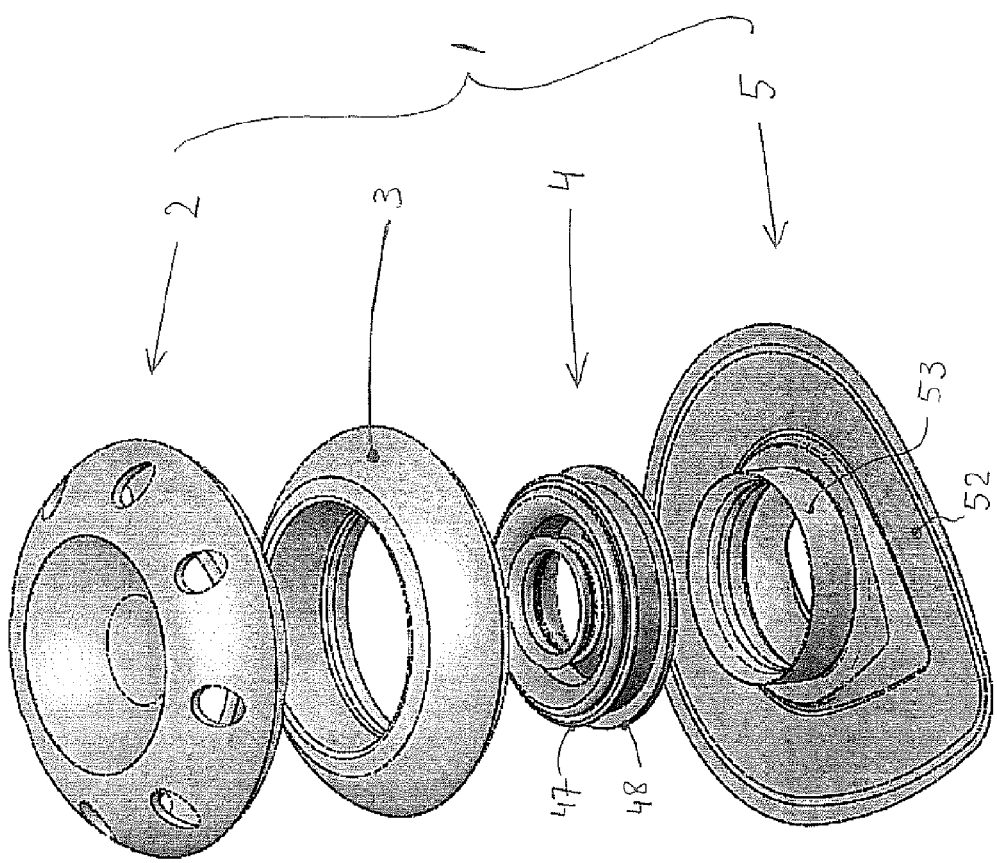

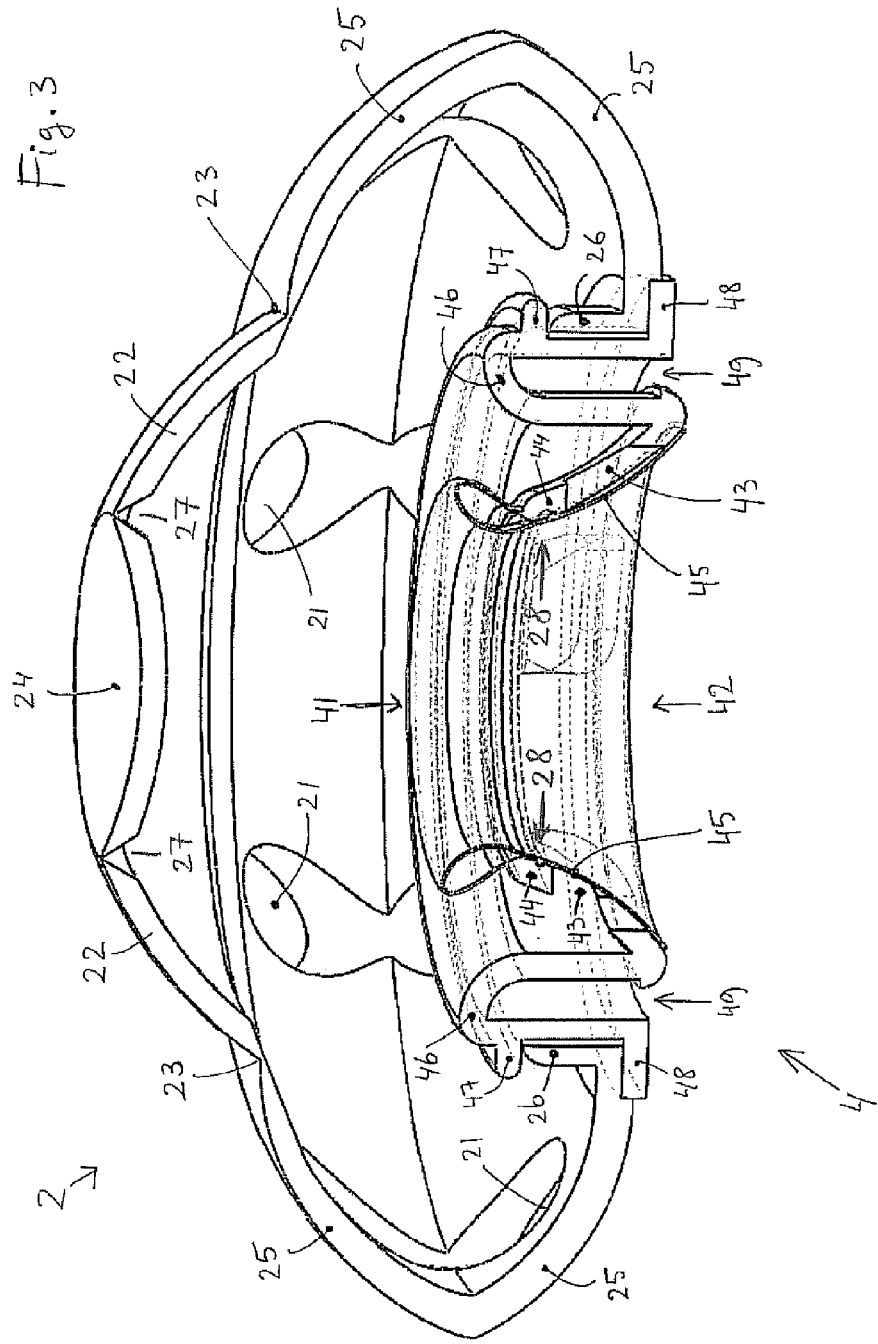

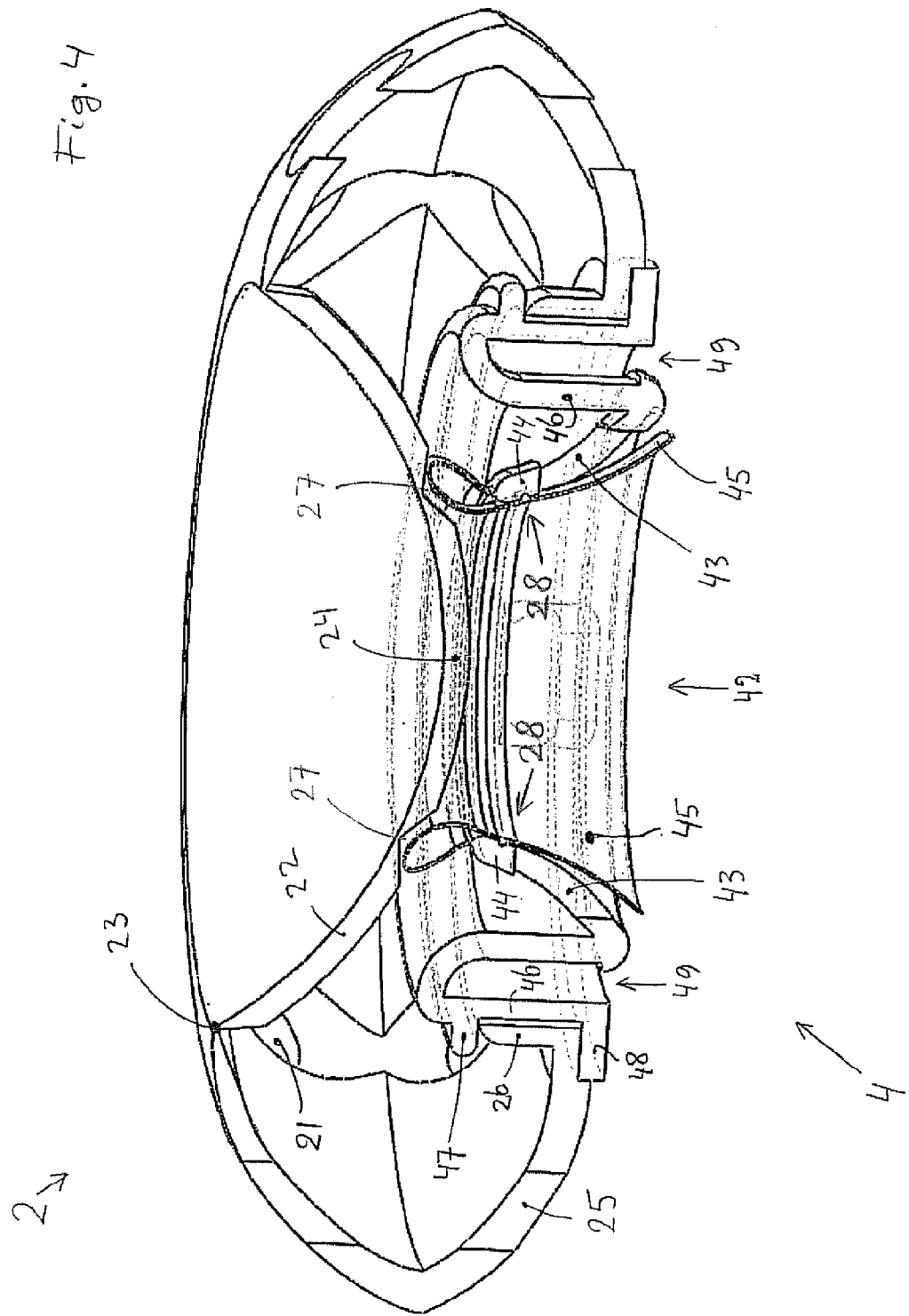

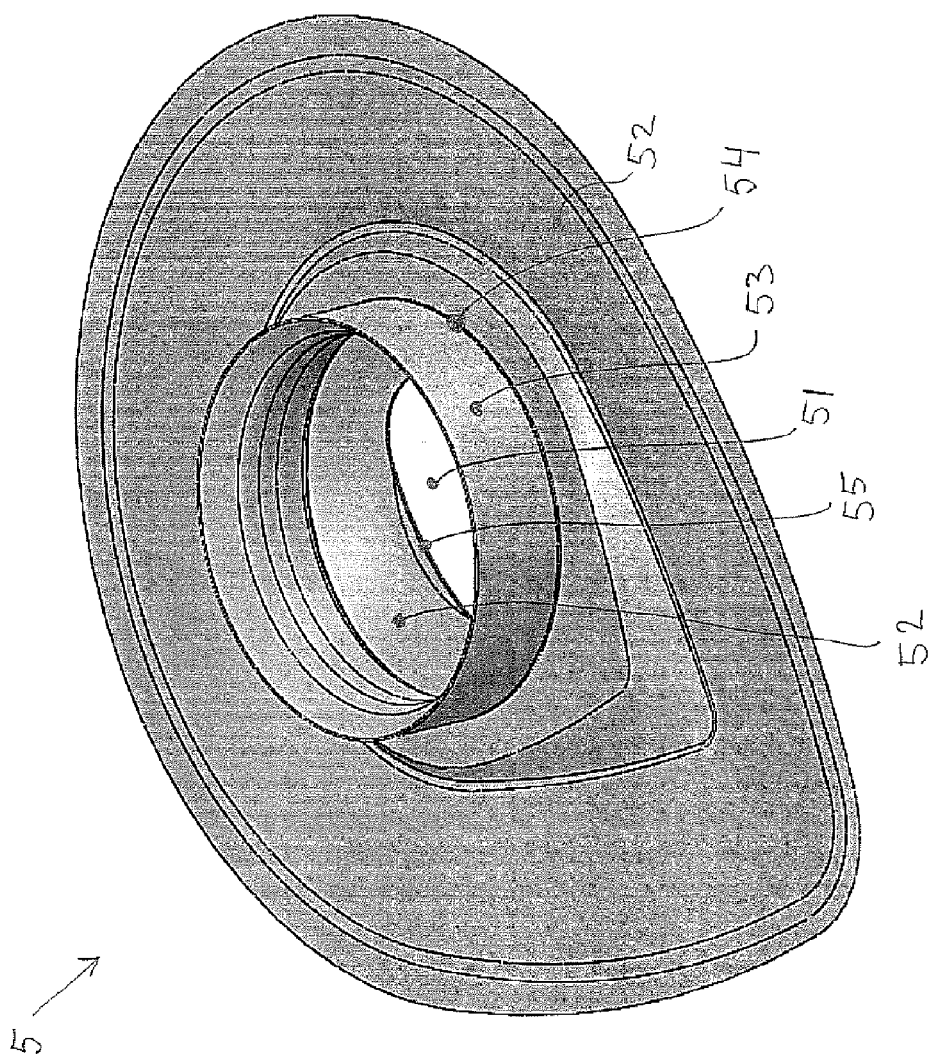

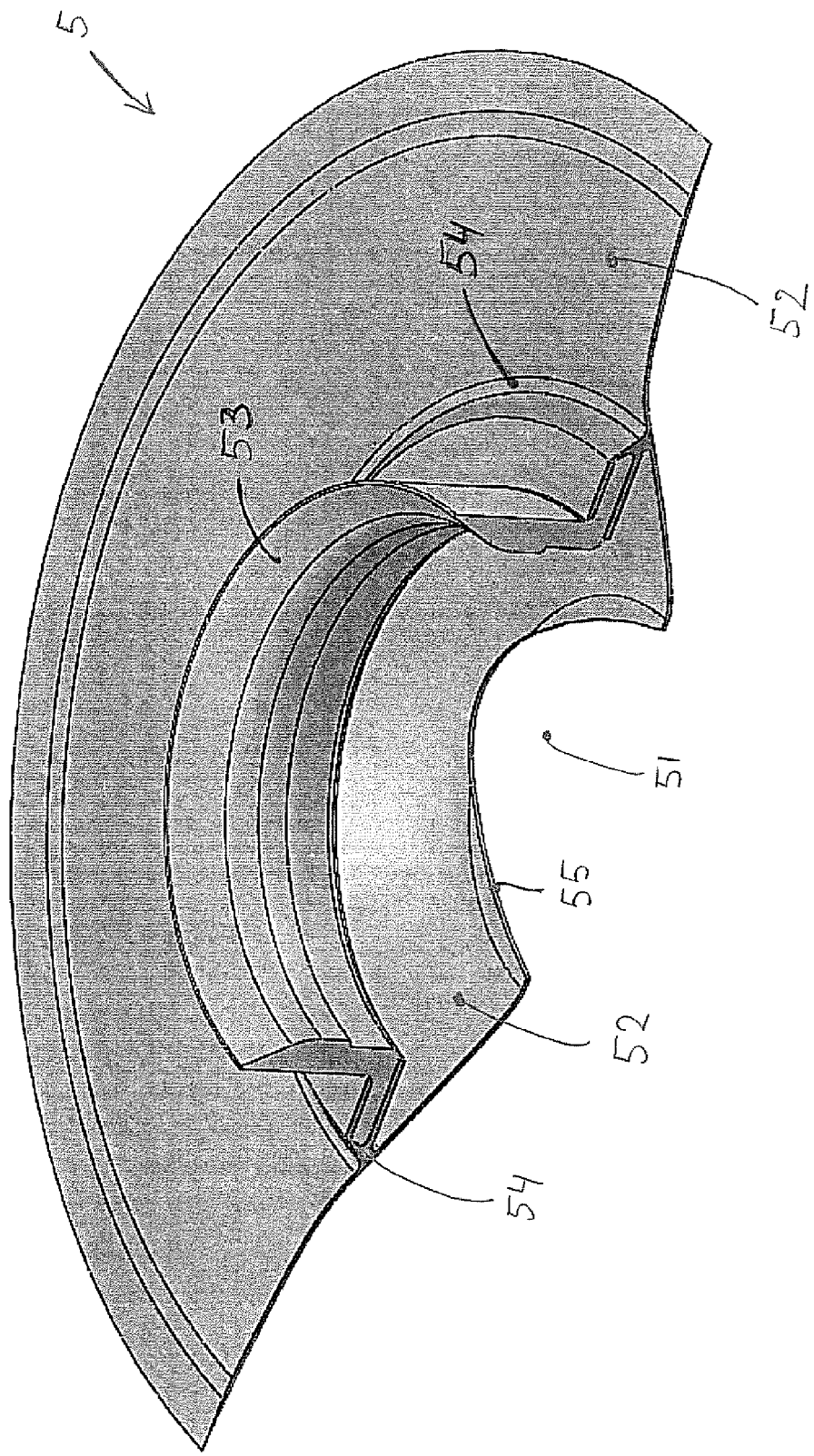

TRACHEOSTOMA VALVE

CROSS-REFERENCE TO RELATED APPLICATION

This application is a United States national phase application of co-pending international patent application number PCT/NL2010/050165, filed Mar. 31, 2010, which claims the benefit of EP Application No. 09157110.9 filed Apr. 1, 2009 and U.S. Provisional Application No. 61/180,956 filed May 26, 2009, each of which is hereby incorporated by reference in its entirety.

BACKGROUND

The invention relates to a tracheostoma valve comprising a main air passage structure provided with a main valve arrangement.

Severe cancer in the laryngeal or hypopharyngeal region often requires a total laryngectomy, i.e. excision of the larynx (including vocal folds). Reconstruction is performed by leading the trachea outside. The trachea then ends in an opening in the neck, the so-called "tracheostoma". After this operation, voice restoration usually takes place by tracheo-oesophageal puncture and the insertion of a one-way valve ("shunt valve") in the puncture. In other words, such a shunt valve is inserted in the wall between the trachea and the oesophagus. By closing the tracheostoma (manually or by means of a so-called "tracheostoma valve"), exhalation air flows through the shunt valve to an air chamber enclosed by soft tissue at the top of the oesophagus, which then starts to vibrate and acts as new "vocal folds".

One of the major problems for the patient who has undergone a laryngectomy and voice rehabilitation concerns the tracheostoma. The tracheostoma attracts attention, especially when the patient has to close it with a thumb or finger in order to speak. Also, stoma closure can be unhygienic and impractical when the patient's hands are dirty. Manual tracheostoma closure is also impossible during certain activities, e.g., while driving a car, eating, or participating in sports. Therefore, several tracheostoma valves have been developed in an attempt to overcome these problems related to manual tracheostoma closure.

Such tracheostoma valves are switchable from a breathing condition into a speaking condition, and vice versa. In the breathing condition the main valve arrangement is in an open position allowing air inhalation and exhalation via the main air passage structure. In the speaking condition the main valve arrangement is in a closed position preventing at least air exhalation via the main air passage structure.

The earliest known tracheostoma valves are of a type in which the tracheostoma valve can be switched, in response to a spurt of exhalation air, from said breathing condition into said speaking condition, while the tracheostoma valve switches back, in response to inhalation, from said speaking condition into said breathing condition. This type of known tracheostoma valves (herein referred to as "exhalation valves") has several drawbacks, such as the following. A portion of the exhalation air that is needed for bringing the valve in speaking condition can not be used anymore for speech production. When one has to inhale again, the valve changes from speaking condition into breathing condition. For continuation of speech, the valve then has to be brought in speaking condition again. Furthermore, such exhalation valves are expensive and susceptible to maintenance because they consist of many parts. They are difficult to operate (small knobs for setting), large, heavy, conspicious and hard to the touch.

More recently, in an attempt to overcome some of these drawbacks, there has been developed another tracheostoma valve type. For this other type, the tracheostoma valve is switchable, in response to a spurt of inhalation air, from said breathing condition into said speaking condition, while the tracheostoma valve is switchable, in response to a spurt of exhalation air, from said speaking condition into said breathing condition. The advantage of this other type of known tracheostoma valves (herein referred to as "inhalation valves") is that all exhalation air is available for speech. Moreover, inhalation precedes speaking, which makes speech more natural. Such a known inhalation valve is disclosed in EP1025874.

The inhalation valve known from EP1025874 has a further advantage in that it provides an ability to inhale during phonation, allowing the patient to extend the duration of speech indefinitely. Hence, this known inhalation valve can automatically stay in the speaking condition until the patient deliberately changes it into the breathing condition. The ability to inhale during phonation is realized in that this known inhalation valve comprises a one-way bypass valve member which in said speaking condition allows for air inhalation therethrough, but prevents air exhalation therethrough.

Though the known inhalation valve thus solves some important disadvantages of the exhalation valve, the known inhalation valve still has several drawbacks. For example, it is still expensive and susceptible to maintenance because it consist of many parts, it is still difficult to operate (small knobs for setting), large, heavy, conspicious and hard to the touch.

SUMMARY

It is an object of the invention to provide at least an alternative tracheostoma valve of said "inhalation" type, and, preferably, to provide such an alternative tracheostoma valve which offers improvements with respect to simplicity and/or compactness and/or reliability and/or softness.

For that purpose, the invention provides a tracheostoma valve according to claim 1. Hence, a tracheostoma valve according to the invention is of said "inhalation valve" type, wherein its main valve arrangement comprises an at least partly flexible bistable wall portion which has a circumferential bordering edge, wherein at least part of the circumferential bordering edge forms a hinging means around which the bistable wall portion is hingeable between a first stable position in which said closed position of the main valve arrangement is attained in that an orifice of the main air passage structure is being blocked, and a second stable position in which said open position of the main valve arrangement is attained in that said orifice is released.

Because of said co-operating bistable wall portion and orifice there are only few and simple parts for realizing the main valve arrangement, rendering compactness and low susceptibility to maintenance. Furthermore, the bistable character of the valve arrangement renders additional reliability of the arrangement. The said flexibility of the bistable wall portion contributes to softness of the tracheostoma valve.

As an intermezzo, it is remarked that U.S. Pat. No. 5,392,775 discloses a tracheostoma valve 10 having some features in common with a tracheostoma valve according to the present invention. More in particular, the known tracheostoma valve 10 has a main valve arrangement comprising a duckbill valve 16 having a flexible bistable wall portion 17.

This flexible portion 17 has a circumferential bordering edge, which forms a hinging means around which the portion 17 is hingeable between two stable positions.

However, the known valve 10 is not a valve of the abovementioned "inhalation" type, since it is not switchable in response to a spurt of inhalation air from the abovementioned breathing condition into the abovementioned speaking condition in the sense of a tracheostoma valve according to the present invention. Instead, when starting off from its breathing condition as shown in FIG. 5 of U.S. Pat. No. 5,392,775, the known valve 10 switches in response to a spurt of inhalation air into one of the conditions as shown in FIG. 3 or FIG. 2 of U.S. Pat. No. 5,392,775. In these conditions of FIG. 3 or 2 the main valve arrangement is not in a closed position and air exhalation is not prevented via the main air passage structure, because of the presence of the air flow passage 59 defined by the two flexible edges 19, 21 of the flexible portion 17. In fact, when starting off from the condition as shown in said FIG. 2, such air exhalation is prevented not until pressure differences resulting from exhalation air have forced the two flexible edges 19, 21 together so as to form a seal 29 shown in the condition of FIG. 4 of U.S. Pat. No. 5,392,775. Thus, only said FIG. 4 represents a speaking condition in the sense of a tracheostoma valve according to the present invention. Because of this delayed prevention of air exhalation via the main air passage structure, the known valve 10 suffers from drawbacks which are similar to those of the valves of the "exhalation" type as defined and discussed above. That is, in each exhalation stroke occurring during a speech session a portion of exhalation air, leaking through the air flow passage 59 and needed for bringing the valve 10 in the speaking condition of said FIG. 4, is wasted in the sense that it can not be used anymore for speech production.

A further difference between the known valve 10 and a valve according to the invention is explained as follows. The only two positions in which the flexible portion 17 of the known valve 10 is stable are the "normal resting position 31" shown in FIG. 2 of U.S. Pat. No. 5,392,775 and the "inverted position" shown in FIG. 5 of U.S. Pat. No. 5,392,775. Note that the position shown in FIG. 4 of U.S. Pat. No. 5,392,775 is not stable. In fact, the position of FIG. 4 merely exists by the grace of external conditions, more specifically the external flow conditions in the form of exhalation air flow that creates the pressure differences forcing the two flexible edges 19, 21 together. In absence of such exhalation air flow, the flexible portion 17 automatically returns to its stable position of FIG. 2. In the stable, normal resting position 31 shown in FIG. 2 air is free to flow in opposing directions through the air flow passage 59 defined by the two flexible edges 19, 21 of the flexible portion 17. In contrast, for a valve according to the invention, the position of the bistable wall portion in which the closed position of the main valve arrangement is attained is a stable position.

In addition to the mentioned drawback relating to wasting portions of exhalation air not available for speech production anymore, the known valve 10 suffers from the further drawback that it is relatively spacious. Especially when seen in axial direction of the tubular section 11 to which the flexible portion 17 is mounted, the flexible portion 17 takes up a lot of space not only in its normal positions (FIGS. 2-4 of U.S. Pat. No. 5,392,775), but also in its inverted position (FIG. 5 of U.S. Pat. No. 5,392,775). This makes the known tracheostoma valve 10, which is based upon the duckbill valve 16, generally impractical for daily use by patients having undergone laryngectomy and reconstruction.

Herewith, the intermezzo regarding the discussion of the tracheostoma valve known from U.S. Pat. No. 5,392,775 is concluded, and we now revert to further aspects of a tracheostoma valve according to the present invention.

Preferably, the bistable wall portion is an integrated part of an at least partly flexible main wall of the tracheostoma valve, wherein the hinging means of the circumferential bordering edge comprises an area of the main wall having locally reduced wall thickness. In this way, the hinging means are, so to speak, implicitly formed by at least part of the bordering edge of the bistable wall portion. This further contributes to the simplicity, compactness and softness of the tracheostoma valve.

Preferably, in operation, the bistable wall portion is arranged such that it is accessible for being touched by a user's finger. Thus, the tracheostoma valve is switchable from the breathing condition into the speaking condition not only in response to a spurt of inhalation air, but also in response to manually pushing the bistable wall portion from the second stable position into the first stable position. Furthermore, when the tracheostoma valve is in its speaking condition and the user wants to speak very loud, the user then is able to prevent an undesirable switching into the breathing condition by manually retaining the bistable wall portion in the first stable position.

Preferably, at least the main air passage structure comprises filtering means arranged for being moisturised by exhalation air and thus for moisturising inhalation air. This assures that inhaled air via the tracheostoma valve has approximately the same humidity as air that is inhaled via upper respiratory ways. Hence, the filtering means functions as an "artificial nose". The filtering means may for example be a foam material, e.g. foamed polyurethane impregnated with calcium chloride.

In a preferable embodiment of the invention, the tracheostoma valve further comprises a bypass air passage structure provided with a one-way bypass valve arrangement which, at least in said speaking condition, allows air inhalation via the bypass air passage structure, but prevents air exhalation via the bypass air passage structure. This bypass air passage structure and one-way bypass valve arrangement provide an ability to inhale during phonation, allowing the patient to extend the duration of speech indefinitely. Hence, this known inhalation valve can automatically stay in the speaking condition until the patient deliberately changes it into the breathing condition.

Preferably, the one-way bypass valve arrangement comprises a first wall portion having at least one bypass opening therein, and a second wall portion forming an at least partly flexible flap, which flap in response to pressure of exhalation air is being pressed against the first wall portion such that the at least one bypass opening is blocked by said second wall portion for said preventing of air exhalation via the bypass air passage structure, and which flap in response to pressure of inhalation air is being released from said at least one bypass opening for said allowing of air inhalation via the bypass air passage structure. Such a first wall portion and second wall portion are a simple, soft and reliable way of realizing the one-way bypass valve arrangement.

Preferably, the first wall portion and the second wall portion are integrated parts of the at least partly flexible main wall of the tracheostoma valve. This further contributes to the compactness of the tracheostoma valve.

In a preferable embodiment of the invention, the tracheostoma valve further comprises an attachment device for attaching and connecting, respectively, the tracheostoma valve to a patient's neck and tracheostoma, respectively, wherein the attachment device comprises a flexible layer structure having a stoma opening therein, the flexible layer structure being arranged for attachment to the patient's neck such that the stoma opening is at the location of the patient's tracheostoma, and a circumferential flange attached to the flexible layer structure, said flange being arranged for connecting the attachment device to other parts of the tracheostoma valve. For said attaching of the attachment device to the patient's neck, it is for example possible that an attachment surface of the flexible layer structure is pre-applied with a suitable adhesive means. Such adhesive means may for example be covered with a foil which can be released from the adhesive means by the patient for exposing the adhesive means for enabling the attachment.

Preferably, the flexible layer structure comprises at least a layer portion that substantially has a funnel shape discharging into the stoma opening, and wherein a circumferential attachment area where the flexible layer structure is attached to the circumferential flange is situated at a distance from a circumferential edge of the stoma opening such that part of said funnel shape extends between said circumferential attachment area and said circumferential stoma opening edge. The funnel shape results in good conformance to the neck and tracheostoma, especially in cases where the patient has a relatively deep tracheostoma. The part of the funnel shape that extends between said circumferential attachment area and said circumferential stoma opening edge prevents tunnelling of air flow between the neck skin and the flexible layer structure and thus prevents air leakeage, peeling of the flexible layer structure and consequent dislodgement of the attachment device from the patient's neck.

It is remarked that an attachment device for attaching and connecting, respectively, a tracheostoma valve to a patient's neck and tracheostoma, respectively, wherein:

the attachment device comprises a flexible layer structure having a stoma opening therein, the flexible layer structure being arranged for attachment to the patient's neck such that the stoma opening is at the location of the patient's tracheostoma, and a circumferential flange attached to the flexible layer structure, said flange being arranged for connecting the attachment device to other parts of the tracheostoma valve; and the flexible layer structure comprises at least a layer portion that substantially has a funnel shape discharging into the stoma opening, and wherein a circumferential attachment area where the flexible layer structure is attached to the circumferential flange is situated at a distance from a circumferential edge of the stoma opening such that part of said funnel shape extends between said circumferential attachment area and said circumferential stoma opening edge; may, with similar effects and advantages, be used with or be part of other types of tracheostoma valves than just the tracheostoma valves having the features disclosed herein. Such an attachment device may, for example, be used with or be part of various other types of "inhalation valves" and also of various types of "exhalation valves".

BRIEF DESCRIPTION OF THE DRAWINGS

Further details, aspects and embodiments of the invention will be described, by way of example only, with reference to the schematic figures in the enclosed drawing.

FIG. 1 shows, in perspective view, an example of an embodiment of an assembled tracheostoma valve according to the invention, the tracheostoma valve being in its breathing condition.

FIG. 2 shows, in perspective view, the tracheostoma valve of FIG. 1 in a disassembled condition.

FIG. 3 shows a perspective view at some cross-sected parts of the tracheostoma valve of FIG. 1, the bistable wall portion being in its second stable position in which the tracheostoma valve is in its breathing condition.

FIG. 4 shows the cross-sected parts of FIG. 3 in similar view, however with the bistable wall portion being in its first stable position in which the tracheostoma valve is in its speaking condition.

FIG. 5 shows, in perspective view, the attachment device of the tracheostoma valve of FIG. 1.

FIG. 6 shows a perspective view at the attachment device of FIG. 5, when cross-sected.

DETAILED DESCRIPTION

FIGS. 1 and 2 show an example of an embodiment of a tracheostoma valve 1 according to the invention. The shown tracheostoma valve 1 comprises a cap 2, a filtering means 3, a cap seat 4 and an attachment device 5. Note that, for simplicity, the filtering means 3 is not shown in FIGS. 3 and 4.

The cap 2 comprises a flexible main wall which has a general shape which is more or less like the shape of a dome. The flexible main wall comprises wall portions 22, 24, 25, wherein the wall portion 25 has a circumferential connection flange 26 (see FIGS. 3 and 4) for connecting the cap 2 to the cap seat 4. The wall portion 25 has a number of breathing openings 21 therein. In the shown example, some of the breathing openings 21 are situated relative to one another at circumferentially spaced apart locations. The shown filtering means 3, for example a foam material, is substantially ring shaped and, in operation, is coaxially placed in the dome shaped cap 2. The cap seat 4 comprises a circumferential, flexible cap seat wall comprising wall portions 44, 45, 46. The wall portion 46 has two circumferential connection flanges 47 and 48 arranged for co-operation with the connection flange 26 of the cap 2 for interconnecting the cap 2 and the cap seat 4, see FIGS. 3 and 4. As shown in FIGS. 3 and 4, the flexible cap seat wall furthermore forms an air passage way 42 and orifice 41. Also, the wall portion 46 forms a circumferential recess 49. The attachment device 5 comprises a circumferential flange 53 arranged for co-operation with the circumferential recess 49 of the cap seat 4 for interconnecting the cap seat 4 and the attachment device 5. As shown in FIGS. 5 and 6, the attachment device 5 further comprises a flexible layer 52 having a stoma opening 51 therein.

The openings 21, the filtering means 3, the orifice 41, the air passage way 42 and the stoma opening 51 are part of the main air passage structure of the tracheostoma valve 1. The main valve arrangement of the tracheostoma valve 1 comprises the two wall portions 22, 24 of the cap 2, which two portions together form a flexible bistable wall portion which has a circumferential bordering edge 23. The circumferential bordering edge forms a hinging means 23 around which the bistable wall portion 22, 24 is hingeable between a first stable position and a second stable position. In the first stable position (shown in FIG. 4) the closed position of the main valve arrangement is attained in that the orifice 41 is being blocked by the bistable wall portion 22, 24. In the second stable position (shown in FIG. 3) the open position of the main valve arrangement is attained in that the bistable wall portion 22, 24 is releasing the orifice 41.

By means of the main air passage structure 21, 3, 41, 42, 51 and the main valve arrangement 22, 23, 24, 41, the tracheostoma valve 1 is switchable in response to a spurt of inhalation air from the breathing condition into the speaking condition, while the tracheostoma valve is switchable in response to a spurt of exhalation air from the speaking condition into the breathing condition. The mechanisms responsible for such switchings are as follows. A spurt of inhalation air in the breathing condition of FIG. 3 causes an underpressure on the interior side of the bistable wall portion 22, 24 relative to the (higher) pressure on the exterior side of the bistable wall portion. The resulting pressure difference causes the bistable wall portion to hinge from its second stable position shown in FIG. 3 into its first stable position shown in FIG. 4. On the other hand, a spurt of exhalation air in the speaking condition of FIG. 4 causes an overpressure on the interior side of the bistable wall portion relative to the (lower) pressure on the exterior side of the bistable wall portion. The resulting pressure difference causes the bistable wall portion to hinge from its first stable position shown in FIG. 4 into its second stable position shown in FIG. 3.

In the shown example, the bistable wall portion 22, 24 is an integrated part of the flexible main wall 22, 24, 25, wherein the hinging means 23 of the circumferential bordering edge 23 comprises an area of the main wall 22, 24, 25 having locally reduced wall thickness.

In the shown example, the bistable wall portion 22, 23, 24 is arranged such that it is accessible for being touched by a user's finger.

The tracheostoma valve 1 further comprises a bypass air passage structure provided with a one-way bypass valve arrangement which, at least in said speaking condition, allows air inhalation via the bypass air passage structure, but prevents air exhalation via the bypass air passage structure.

The one-way bypass valve arrangement comprises a first wall portion, in the form of the abovementioned wall portion 44, and a second wall portion, in the form of the abovementioned wall portion 45. The first wall portion 44 has a number of bypass openings 43 therein. The bypass openings 43 may for example be situated relative to one another at circumferentially spaced apart locations of the first wall portion 44. The second wall portion 45 forms an at least partly flexible flap. In response to pressure of exhalation air, the flap 45 is being pressed against the first wall portion 44 such that the at least one bypass opening 43 is blocked by the flap 45 for said preventing of air exhalation via the bypass air passage structure. In response to pressure of inhalation air, the flap 45 is being released from said at least one bypass opening 43 for allowing air inhalation via the bypass air passage structure.

Some more detailed aspects of the circumferential flexible cap seat wall comprising the wall portions 44, 45 and 46, as used in the shown example, are explained as follows. At first, it is remarked that this flexible cap seat wall has been manufactured as a single integrated piece, for example by moulding. This contributes considerably to the simplicity of the tracheostoma valve. It can be seen from FIGS. 3 and 4 that the wall thickness of the second wall portion 45 is smaller than the wall thickness of the wall portions 44 and 46. Also, FIGS. 3 and 4 show that the orifice 41 is formed by a folding area of the second wall portion 45. That is, the second wall portion 45 was moulded in unfolded condition and, after it was moulded, was folded-back at said folding area. This folding-back operation has created, at the location of the border of the orifice 41, a circumferential air chamber enveloped by the folded-back folding area of the second wall portion 45. The folding area with enveloped air chamber functions as a resilient sealing means for the first stable position of the bistable wall portion 22, 24 in which the closed position of the main valve arrangement is attained in that the orifice 41 of the main passage structure is being blocked, see FIG. 4. Note that in FIG. 4 the folded-back folding area is received in a circumferential groove 27 formed by the shown living hinge 27 between the wall portions 22 and 24 of the bistable wall portion. Said resilient sealing means takes care that, in the shown speaking condition of FIG. 4, a sealing engagement is preserved during moderate movements of the bistable wall portion resulting for example from moderate overpressures on the interior side of the bistable wall portion occurring during normal speaking conditions (hence without producing a spurt of exhalation air). Thus, in fact, the resilient sealing means provide a sealing engagement that remains effective during slight movements of the bistable wall portion 22, 24. Note that, at the locations 28 indicated in FIGS. 3 and 4, the second wall portion 45 may for example have a circumferential ridge that may be received in a circumferential groove in the first wall portion 44 for keeping the folded-back folding area of the first wall portion 45 in place under varying speaking pressures.

As mentioned, the tracheostoma valve according to the invention further comprises the attachment device 5 for attaching and connecting, respectively, the tracheostoma valve 1 to a patient's neck and tracheostoma, respectively, wherein the attachment device comprises a flexible layer structure 52 having a stoma opening 51 therein, the flexible layer structure being arranged for attachment to the patient's neck such that the stoma opening is at the location of the patient's tracheostoma, and a circumferential flange 53 attached to the flexible layer structure 52, said flange being arranged for connecting the attachment device 5 to other parts of the tracheostoma valve 1. In the shown example, the flexible layer structure is formed by the single flexible layer 52. Preferably, the circumferential flange 53 is rigid or at least less flexible than the flexible layer 52. It is remarked that instead of the single layer 52, the flexible layer structure may also have a multilayer structure. Furthermore, it is remarked that the planform of the shown flexible layer 52 may have various forms, such as circular, elliptical, etcetera. In the shown example, the planform has an "egg-like" shape, intended to be placed on the patient's neck in an orientation in which the "top of the egg" is pointing towards the patient's head.

In FIGS. 5 and 6 it can be seen that the flexible layer 52 comprises at least a layer portion that substantially has a funnel shape discharging into the stoma opening 51, and that a circumferential attachment area 54 where the flexible layer structure is attached to the circumferential flange 53 is situated at a distance from a circumferential edge 55 of the stoma opening 51 such that part of said funnel shape extends between said circumferential attachment area 54 and said circumferential stoma opening edge 55.

In the foregoing specification, the invention has been described with reference to specific examples of embodiments of the invention. It will, however, be evident that various modifications and changes may be made therein without departing from the broader scope of the invention as set forth in the appended claims.

For example, in the shown example, the full bistable wall portion is flexible. It is however possible to apply a bistable wall portion which also has non-flexible parts. Furthermore, in the shown example, the openings 21 are not intersecting the circumferential bordering edge 23. Instead, such intersecting may be possible, in which case only the not intersected parts of the circumferential bordering edge 23 form hinging means. Also, in the shown example, in the first stable position (shown in FIG. 4) the closed position of the main valve arrangement is attained in that the orifice 41 is being blocked by direct abutting contact of the bistable wall portion 22, 24 against the boundary of the orifice 41. Instead, indirect blocking of the orifice is possible, for example in that the bistable wall portion in its first stable position provides for blocking of the orifice via a separate other element of the main valve arrangement.

Furthermore, the cap and cap seat may be integrally manufactured, for example in the form of a single, circumferential flexible wall, in which case the flanges 26, 47 and 48 are not necessary anymore. Similarly, the attachment device may be integrally manufactured with the cap seat (and cap).

The flexible character of its parts makes the tracheostoma valve foldable, which is convenient for many purposes, for example for storage in a ladies handbag, for facilitating the interchanging of the filtering means, or for machine washing together with clothing. The total tracheostoma valve may for example be made flexible, or it may be made totally flexible apart from a stiff circumferential flange of the attachment device.

Also, the cap may have various other shapes than the shown dome shape.

The flexible wall(s)/layer(s) used in a tracheostoma valve according to the invention may be made of various materials, for example elastomeric materials, such as silicone rubber. These flexible wall(s)/layer(s) may have various, locally varying thickness distributions, in which local thicknesses may generally be very small, such as in the order of less than 1.0 millimeters or less than 0.5 millimeters or less than 0.2 millimeters.

However, other modifications, variations and alternatives are also possible. The specifications and drawings are, accordingly, to be regarded in an illustrative rather than in a restrictive sense.

The invention claimed is:

1. Tracheostoma valve comprising a main air passage structure provided with a main valve arrangement, wherein the tracheostoma valve is switchable in response to a spurt of inhalation air from a breathing condition, in which the main valve arrangement is in an open position allowing air inhalation and exhalation via the main air passage structure, into a speaking condition, in which the main valve arrangement is in a closed position preventing at least air exhalation via the main air passage structure, while the tracheostoma valve is switchable in response to a spurt of exhalation air from said speaking condition into said breathing condition, wherein the main valve arrangement comprises an at least partly flexible bistable wall portion which has a circumferential bordering edge, wherein at least part of the circumferential bordering edge forms a hinge around which the bistable wall portion is hingeable between a first stable position in which said closed position of the main valve arrangement is attained in that an orifice of the main air passage structure is being blocked, and a second stable position in which said open position of the main valve arrangement is attained in that said orifice is released.

2. Tracheostoma valve according to claim 1, wherein the bistable wall portion is an integrated part of an at least partly flexible main wall of the tracheostoma valve, wherein the hinge of the circumferential bordering edge comprises an area of the main wall having locally reduced wall thickness.

3. Tracheostoma valve according to claim 1 or 2, wherein, in operation, the bistable wall portion is arranged such that it is accessible for being touched by a user's finger.

4. Tracheostoma valve according to claim 1, wherein at least the main air passage structure comprises a filter arranged for being moisturised by exhalation air and thus for moisturising inhalation air.

5. Tracheostoma valve according to claim 1, further comprising a bypass air passage structure provided with a one-way bypass valve arrangement which, at least in said speaking condition, allows air inhalation via the bypass air passage structure, but prevents air exhalation via the bypass air passage structure.

6. Tracheostoma valve according to claim 5, wherein the one-way bypass valve arrangement comprises a first wall portion having at least one bypass opening therein, and a second wall portion forming an at least partly flexible flap, which flap in response to pressure of exhalation air is being pressed against the first wall portion such that the at least one bypass opening is blocked by said second wall portion for said preventing of air exhalation via the bypass air passage structure, and which flap in response to pressure of inhalation air is being released from said at least one bypass opening for said allowing of air inhalation via the bypass air passage structure.

7. Tracheostoma valve according to claim 6, wherein the bistable wall portion is an integrated part of an at least partly flexible main wall of the tracheostoma valve, wherein the hinge of the circumferential bordering edge comprises an area of the main wall having locally reduced wall thickness and wherein the first wall portion and the second wall portion are integrated parts of the at least partly flexible main wall of the tracheostoma valve.

8. Tracheostoma valve according to claim 1, further comprising an attachment device for attaching and connecting, respectively, the tracheostoma valve to a patient's neck and tracheostoma, respectively, wherein the attachment device comprises a flexible layer structure having a stoma opening therein, the flexible layer structure being arranged for attachment to the patient's neck such that the stoma opening is at the location of the patient's tracheostoma, and a circumferential flange attached to the flexible layer structure, said flange being arranged for connecting the attachment device to other parts of the tracheostoma valve.

9. Tracheostoma valve according to claim 8, wherein the flexible layer structure comprises at least a layer portion that substantially has a funnel shape discharging into the stoma opening, and wherein a circumferential attachment area where the flexible layer structure is attached to the circumferential flange is situated at a distance from a circumferential edge of the stoma opening such that part of said funnel shape extends between said circumferential attachment area and said circumferential stoma opening edge.

* * * * *